(12) United States Patent
Kuhnen et al.

(10) Patent No.: US 10,527,585 B2
(45) Date of Patent: Jan. 7, 2020

(54) ELECTROMAGNETIC DRIVING/RECEIVING UNIT FOR A FIELD DEVICE OF AUTOMATION TECHNOLOGY

(71) Applicant: Endress+Hauser GmbH+Co. KG, Maulburg (DE)

(72) Inventors: Raphael Kuhnen, Schliengen (DE); Dietmar Frühauf, Lörrach (DE)

(73) Assignee: Endress+Hauser SE+Co. KG, Maulburg (DE)

( * ) Notice: Subject to any disclaimer, the term of this patent is extended or adjusted under 35 U.S.C. 154(b) by 76 days.

(21) Appl. No.: 15/560,281

(22) PCT Filed: Feb. 15, 2016

(86) PCT No.: PCT/EP2016/053130
§ 371 (c)(1),
(2) Date: Sep. 21, 2017

(87) PCT Pub. No.: WO2016/150620
PCT Pub. Date: Sep. 29, 2016

(65) Prior Publication Data
US 2018/0074018 A1   Mar. 15, 2018

(30) Foreign Application Priority Data
Mar. 25, 2015 (DE) .................. 10 2015 104 533

(51) Int. Cl.
*G01N 29/036*   (2006.01)
*G01N 29/02*    (2006.01)
(Continued)

(52) U.S. Cl.
CPC ....... *G01N 29/036* (2013.01); *G01F 23/2968* (2013.01); *G01N 9/002* (2013.01);
(Continued)

(58) Field of Classification Search
CPC .... G01N 29/036; G01N 29/022; G01N 9/002; G01N 2009/006; G01N 11/16; G01F 23/2968
(Continued)

(56) References Cited

U.S. PATENT DOCUMENTS

| 3,625,058 A | 12/1971 | Dress et al. |
| 2019/0226901 A1* | 7/2019 | Kuhnen .................... G01F 1/05 |
| 2019/0257683 A1* | 8/2019 | Kuhnen .............. G01F 23/2966 |

FOREIGN PATENT DOCUMENTS

| CN | 1423582 A | 6/2003 |
| CN | 1969590 A | 5/2007 |

(Continued)

*Primary Examiner* — Lisa M Caputo
*Assistant Examiner* — Rose M Miller
(74) *Attorney, Agent, or Firm* — Christopher R. Powers; PatServe

(57) ABSTRACT

An electromechanical transducer unit for a field device includes a membrane embodied to execute mechanical oscillations, two rods perpendicular to the membrane and secured to the membrane, a housing, wherein the membrane forms at least one portion of a wall of the housing, and wherein the two rods extend into the housing interior, two magnets, wherein each magnet is secured in an end region away from the membrane to a different one of the two rods, and a coil with a core, wherein the coil is secured above the magnets within the housing, and is contactable with an electrical, alternating current signal, wherein the coil is embodied to produce a magnetic field that causes the two rods via the two magnets to execute mechanical oscillations, and wherein the two rods are secured to the membrane such that oscillations of the membrane result from oscillations of the two rods.

16 Claims, 5 Drawing Sheets

(51) Int. Cl.
*G01N 11/16* (2006.01)
*G01F 23/296* (2006.01)
*G01N 9/00* (2006.01)

(52) U.S. Cl.
CPC ........... *G01N 11/16* (2013.01); *G01N 29/022* (2013.01); *G01N 2009/006* (2013.01)

(58) Field of Classification Search
USPC ...................................... 73/579, 643, 290 V
See application file for complete search history.

(56) References Cited

FOREIGN PATENT DOCUMENTS

| | | | |
|---|---|---|---|
| DE | 10050299 A1 | 4/2002 | |
| DE | 10057974 A1 | 5/2002 | |
| DE | 102005015547 A1 | 10/2006 | |
| DE | 102006033819 A1 | 1/2008 | |
| DE | 102006034105 A1 | 1/2008 | |
| DE | 102007013557 A1 | 2/2008 | |
| DE | 102007043811 A1 | 3/2009 | |
| DE | 102008044186 A1 * | 6/2010 | ........... G01F 1/8418 |
| DE | 102009026685 A1 | 12/2010 | |
| DE | 102009028022 A1 | 2/2011 | |
| DE | 102010030982 A1 | 1/2012 | |
| EP | 0248995 A1 | 12/1987 | |
| EP | 0949489 A1 | 10/1999 | |
| EP | 2209110 A1 | 7/2010 | |
| EP | 2801799 A1 | 11/2014 | |
| GB | 837480 A * | 6/1960 | ............. G01R 27/32 |
| SU | 1163275 A * | 6/1985 | ............. G01P 15/08 |
| WO | 2005085770 A2 | 9/2005 | |
| WO | 2007113011 A1 | 10/2007 | |
| WO | 2007114950 A2 | 10/2007 | |
| WO | 2012115520 A1 | 8/2012 | |
| WO | 2015028179 A1 | 3/2015 | |

* cited by examiner

ELECTROMAGNETIC DRIVING/RECEIVING UNIT FOR A FIELD DEVICE OF AUTOMATION TECHNOLOGY

CROSS-REFERENCE TO RELATED APPLICATIONS

The present application is related to and claims the priority benefit of German Patent Application No. 10 2015 104 533.8, filed on Mar. 25, 2015 and International Patent Application No. PCT/EP2016/053130, filed on Feb. 15, 2016, the entire contents of which are incorporated herein by reference.

TECHNICAL FIELD

The invention relates to an electromechanical transducer unit for a field device of automation technology and to an apparatus for determining and/or monitoring at least one process variable of a medium in a containment, which apparatus comprises at least one electromechanical transducer unit of the invention. The process variable is, for example, the fill level or the flow of the medium or also its density or viscosity. The medium is located, for example, in a container, a tank, or even in a pipeline.

BACKGROUND

In automation technology, the most varied of field devices are applied for determining and/or monitoring at least one process variable, especially a physical or chemical, process variable. In such case, for example, fill level measuring devices, flow measuring devices, pressure- and temperature measuring devices, pH-redox potential measuring devices, conductivity measuring devices, etc., register the corresponding process variables, fill level, flow, pressure, temperature, pH-value, conductivity, etc. The respective measuring principles are known from a large number of publications.

A field device includes typically at least one sensor unit, coming, at least partially and at least at times, in contact with the process, and an electronics unit, which serves, for example, for signal registration, —evaluation and/or—feeding. Referred to as field devices in the context of present invention are, in principle, all measuring devices, which are applied near to the process and which deliver, or process, process relevant information, thus also remote I/Os, radio adapters, and, generally, electronic components, which are arranged at the field level. A large number of such field devices are produced and sold by the applicant.

Electromechanical transducer units are used quite often in field devices. For example, they are used in vibronic sensors, such as, for example, vibronic fill level- or flow measuring devices, however, also in ultrasonic, fill-level measuring devices or ultrasonic, flow measuring devices. To explore separately and in detail each and every such field device and its measuring principle, where an electromechanical transducer unit of the invention could be used, would be to go beyond what is necessary. Therefore, the description has been limited, by way of example, to fill level measuring devices with an oscillatable unit. Based on this description, it will be apparent to those skilled in the art how the invention can be applied in other areas of use.

The oscillatable unit of such a fill-level measuring device, also referred to as a vibronic sensor, is, for example, an oscillatory fork, single rod or membrane. The oscillatable unit is driven during operation by means of a driving/receiving unit, usually in the form an electromechanical transducer unit, to excite the oscillatable unit, such that it executes mechanical oscillations. Examples include piezoelectric, electromagnetic or also magnetostrictive driving/receiving units. Corresponding field devices are produced in great variety by the applicant and sold, for example, under the marks, LIQUIPHANT and SOLIPHANT. The underpinning measuring principles are fundamentally known. The driving/receiving unit excites the mechanically oscillatable unit by means of an electrical exciting signal to execute mechanical oscillations. Conversely, the driving/receiving unit can receive mechanical oscillations of the mechanically oscillatable unit and convert them into an electrical, received signal. The driving/receiving unit can be either a separate drive unit and a separate receiving unit, or a combined driving/receiving unit.

The most varied of both analog as well as also digital methods have been developed for exciting the mechanically oscillatable unit. In many cases, the driving/receiving unit is part of a feedback, electrical, oscillatory circuit, by means of which the exciting of the mechanically oscillatable unit to execute mechanical oscillations occurs. For example, for a resonant oscillation, the oscillatory circuit condition must be fulfilled, according to which the amplification factor is ≥1 and all phases arising in the oscillatory circuit sum to a multiple of 360°. This means that a certain phase shift must be assured between the exciter signal and the received signal. For this, the most varied of solutions are known. In principle, the setting of the phase shift can be performed, for example, by application of a suitable filter, or also be controlled by means of a control loop to a predeterminable phase shift, the desired value. Known from DE102006034105A1, for example, is to use a tunable phase shifter. The additional integration of an amplifier with adjustable amplification factor for additional control of the oscillation amplitude is, in contrast, described in DE102007013557A1. DE102005015547A1 proposes the application of an allpass filter. The setting of the phase shift is, moreover, possible by means of a so-called frequency sweep, such as disclosed, for example, in DE102009026685A1, DE102009028022A1, and DE102010030982A1. The phase shift can, however, also be controlled by means of a phase locked loop (PLL) to a predeterminable value. Such an excitation method is subject matter of DE00102010030982A1.

Both the exciter signal as well as also the received signal are characterized by frequency, amplitude and/or phase. Changes in these variables are then usually taken into consideration for determining the respective process variable, such as, for example, a predetermined fill level of a medium in a container, or also the density and/or viscosity of a medium. In the case of a vibronic limit level switch for liquids, for example, it is distinguished, whether the oscillatable unit is covered by the liquid or freely oscillating. These two states, the free state and the covered state, are, in such case, distinguished, for example, based on different resonance frequencies, thus a frequency shift, or based on a damping of the oscillation amplitude.

Density and/or viscosity can, in turn, be ascertained with such a measuring device only when the oscillatable unit is covered by the medium. Known from DE10050299A1, DE102006033819A1 and DE102007043811A1 is to determine the viscosity of a medium based on the phase frequency curve ($\phi=g(f)$). This procedure is based on the dependence of the damping of the oscillatable unit on the viscosity of the medium. In order to eliminate the influence of density on the measuring, the viscosity is determined based on a frequency change caused by two different values for the phase, thus by means by a relative measurement. For determining and/or monitoring the density of a medium, in contrast, according to DE10057974A1, the influence of at least one disturbing variable, for example, the viscosity, on the oscillation frequency of the mechanically oscillatable unit is ascertained and compensated. In DE102006033819A1, it is, furthermore, proposed to set a predeterminable phase shift between the exciter signal and the received signal, in the case of which effects of changes of the viscosity of the medium on the mechanical oscillations of the mechanically oscillatable unit are negligible. At this phase shift, an empirical formula for determining the density can be established.

The driving/receiving unit is, as already mentioned, as a rule, embodied as an electromechanical transducer unit. Often, it includes at least one piezoelectric element in the most varied of embodiments. Using the piezoelectric effect, a high efficiency can be achieved. In such case, meant is the efficiency of the changing of the electrical energy into mechanical energy. Corresponding piezoceramic materials based on LZT (lead zirconate titanate) are, normally, suitable for use at temperatures up to 300° C. There are piezoceramic materials, which keep their piezoelectric properties at temperatures above from 300° C.; these have all, however, the disadvantage that they are significantly less efficient than the materials based on LZT. For use in vibronic sensors, these high temperature materials are, moreover, only conditionally suitable due to the large differences in the coefficients of thermal expansion between metals and ceramic materials. Because of their function as force providers, the at least one piezoelectric element must be connected for force transmission to a membrane, which is part of the oscillatable unit. Especially in the case of high temperatures, however, often large mechanical stresses are experienced, which can lead to a breaking of the piezoelectric element and, associated therewith, a total failure of the sensor.

An alternative, which can be better suitable for use at high temperatures, is represented by the so-called electromagnetic driving/receiving units, such as, for example, described in WO 2007/113011 and WO 2007/114950 A1. The changing of electrical energy into mechanical energy occurs, in such case, via a magnetic field. A corresponding electromechanical transducer unit includes at least one coil and a permanent magnet. By means of the coil, an alternating magnetic field is produced passing through the magnet, and via the magnet a periodic force is transmitted to the oscillatable unit. Usually, the transmission of this periodic force occurs via the solenoid principle, where the mobile core contacts the membrane centrally.

Since in the case of an electromagnetic driving/receiving unit, no force transmitting connection with the membrane of the oscillatable unit is necessary, such can be used, in comparison with piezoelectric transducer units, in an expanded temperature range, especially between −200° C. and 500° C. However, as a result of the absence of a force transmitting connection, usually the efficiency is significantly less than in the case of piezoelectric driving/receiving units. While an electromagnetic driving/receiving unit can develop relatively high forces in the region of the membrane, the deflection of the oscillatory fork is comparatively small as a result of there being no force transmitting connection between membrane and drive. As a result, more energy is required for an electromagnetic driving/receiving unit in comparison to a piezoelectric driving/receiving unit, a situation which makes use of a corresponding sensor in explosion-endangered regions problematic.

SUMMARY

An object of the present invention is to provide an electromagnetic driving/receiving unit, or an electromechanical transducer unit, having at least one coil and one magnet and distinguished by an increased efficiency.

This object is achieved according to the invention by an electromechanical transducer unit for a field device of automation technology, comprising
  a membrane, which can be caused to execute mechanical oscillations,
  two rods perpendicular to the membrane and secured to the membrane,
  a housing, wherein the membrane forms at least one portion of a wall of the housing, and wherein the two rods extend into the housing interior,
  two magnets, wherein each magnet is secured in the end region facing away from the membrane to a different one of the two rods, and
  a coil with a core, wherein the coil is secured above the magnets within the housing and is contactable with an electrical, alternating current signal,
wherein the coil is embodied to produce a magnetic field, which magnetic field causes the two rods by means of the two magnets to execute mechanical oscillations, and wherein the two rods are secured to the membrane in such a manner that oscillations of the membrane result from the oscillations of the two rods.

The changing of electrical into mechanical energy occurs via a magnetic alternating field, by means of which the two rods are cause to execute oscillations. The rods behave thus as a mechanical resonator. The oscillatory movement occurs, in such case, transversely, or perpendicularly, to the longitudinal axis of the two rods. By connection, especially a force transmitting connection, with the membrane, the oscillatory movements are transmitted to the membrane, which likewise executes an oscillatory movement.

The electromechanical transducer unit of the invention is best suitable for use in an expanded temperature range, especially for use at high temperatures. Since the two rods are connected in an end region directly with the membrane and form their own resonator, the efficiency of an electromechanical transducer unit of the invention is increased compared with the variants from the state of the art mentioned in the introduction of the description. In spite of this, the structural construction of an electromechanical transducer unit of the invention is comparatively simple.

In a preferred embodiment, the magnets are Alnico magnets. Alnico magnets are occasionally also referred to as steel magnets. Of concern here are alloys of iron, aluminum, nickel, copper and cobalt, from which permanent magnets are produced by casting techniques or by means of sinter processes. Among other things, such magnets are distinguished by a high remanence flux density (about 0.6-1.3 T) as well as by a high Curie temperature of 700-850° C., which permits applications in a temperature range at least up to 500° C. An interesting alternative, in given cases, is represented by rare earth magnets, which are formed essentially of iron metals and rare earth metals. For example, samarium-cobalt is, currently, applicable at temperatures up to 350°; however, research efforts are ongoing to achieve operating temperatures of greater than 500° C. Of course, however, also other magnets can be used for the present invention.

An especially preferred embodiment provides that the core of the coil is part of a pot-shaped armature unit, which has a floor and a peripheral wall, wherein starting from the floor and extending centrally into the interior of the armature unit a stub is secured, wherein the stub forms the core of the coil, and wherein the peripheral wall serves as magnetic field guide back. The peripheral wall extends, for example, up to the rods, which the armature unit should not contact. This embodiment offers, on the one hand, structural advantages, since both the coil core as well as also a field guide back can be provided as a single piece in the form of the armature unit. The field guide back cares, in such case, however, furthermore, also for a magnetic shielding, which further increases the efficiency of the correspondingly embodied, electromechanical transducer unit of the invention.

In such case, it is advantageous that the armature unit be composed of a material with high magnetic permeability, especially iron, cobalt, or cobalt iron, or of a metal glass. As regards high magnetic permeability, especially suited are ferromagnetic materials having at least $\mu>100$. For example, the permeability $\mu$ of cobalt iron lies in the range $\mu_{cobalt\ iron} \approx 10000\text{-}150000$, that for cobalt in the range $\mu_{cobalt} \approx 100\text{-}200$ and for iron it is in the range $\mu_{iron} \approx 300\text{-}10000$. Especially advantageous is when the material for the armature unit has a hysteresis as low as possible. The hysteresis should be at least small enough that the material can exhibit a steady reversal of magnetism corresponding to the frequency of the excitation signal.

Ferromagnetic materials are especially well suited for use at high temperatures. If the requirement for use at especially high temperatures is, in contrast, not the central focus, then metal glasses, whose magnetic permeability lies typically in the range $\mu_{Metglas} \approx 1500\text{-}4000$, are of interest, since these have an especially low hysteresis and, associated therewith, low losses at the reversal of magnetism.

Likewise advantageous is when the two magnets extend contactlessly into the pot-shaped armature unit, and, in the case, in which no magnetic field is present, are located at the same separation from the coil on oppositely lying sides. In this way, the two magnets are completely encased by the magnetic field guide back.

The object of the invention is, furthermore, achieved by an apparatus for determining and/or monitoring at least one process variable of a medium in a containment, comprising
    a sensor unit with at least one electromechanical transducer unit as claimed in at least one of the preceding claims, and
    an electronics unit,
wherein the electromechanical transducer unit is embodied by means of an electrical excitation signal in the form an electrical, alternating current signal, with which the coil is supplied, to excite the sensor unit to execute mechanical oscillations, and to receive mechanical oscillations of the sensor unit and to convert such into an electrical, received signal in the form an electrical, alternating current signal, and wherein the electronics unit is embodied to produce the exciter signal starting from the received signal, and to determine the at least one process variable based at least on the received signal. The driving/receiving unit can, in such case, be either a separate drive unit and a separate receiving unit, or a combined driving/receiving unit.

The oscillations of the oscillatable unit result from oscillations of the two rods. In such case, it is advantageous that the length L of the two rods be selected in such a manner that $L=n\lambda/2+\lambda/4$, wherein $\lambda$ is the wavelength of the waves propagating along the extending rods and n is a natural number. The length of the rods is thus adapted corresponding to a desired excitation frequency and depending on the required temperature decoupling, which results from the spatial separation of the driving/receiving unit from the process.

In an embodiment, the sensor unit includes an oscillatable unit. In this case, the apparatus of the invention is a vibronic sensor.

Another embodiment provides that the oscillatable unit is at least one portion of the membrane, or at least one portion of the membrane as well as at least one oscillatory rod secured thereto. In this case, the oscillatable unit is thus a membrane, a single rod or an oscillatory fork.

The membrane can, on the one hand, be prepared as one-piece. In the case, in which the correspondingly embodied apparatus includes an oscillatable unit, the membrane is then, on the one hand, associated with the electromagnetic transducer unit, but forms, however, simultaneously the oscillatable unit. On the other hand, an embodiment includes that the membrane has two portions connected with one another by force transmitting connection, wherein a first portion is associated with the electromagnetic transducer unit and wherein a second portion is associated with the oscillatable unit. The connection between the two portions can then be produced, for example, by means of a solder-, weld- or adhesive connection.

It is advantageous that the oscillatable unit be arranged in a defined position within the containment, in such a manner that it descends to a determinable immersion depth in the medium. In this way, the process variables, viscosity and/or density, can be determined.

It is likewise advantageous that the process variable is a fill level or the flow of the medium in the containment, or the density or the viscosity of the medium.

In an especially preferred embodiment, the oscillatable unit is an oscillatory fork with two rods, wherein the two rods of the electromechanical transducer unit secured to the membrane and the two oscillatory rods secured to the membrane are arranged oppositely lying and mirror symmetrically to one another with reference to a plane perpendicular to the longitudinal axis through the rods and/or oscillatory rods. In each case, an oscillatory rod and a rod extend thus essentially along the same imaginary line parallel to their two longitudinal axes. Especially, the two rods and the oscillatory rods are arranged in such a manner that they are located with the same separation from the midpoint of the membrane extending perpendicularly to the longitudinal axis of the rods and oscillatory rods. This symmetric arrangement in the case of a vibronic sensor with an oscillatory fork as oscillatable unit achieves an especially high efficiency.

In such case, it is advantageous that the two oscillatory rods and the membrane form a first mechanical resonator, and that the two rods of the electromechanical transducer unit and the membrane form a second mechanical resonator. Then, the first and the second resonators are mechanically coupled with one another by means of the membrane, wherein the frequency of the excitation signal is selected in such a manner that the first and second resonators oscillate in an antisymmetric, oscillatory mode with reference to the membrane extending perpendicularly to the longitudinal axis of the rods and/or oscillatory rods. The oscillatory rods, rods and the membrane form thus a coupled oscillatory system, wherein the coupling is determined by the membrane. In such a coupled oscillatory system, two resonance frequencies occur. To the extent that these resonance frequencies lie sufficiently close to one another, the rods and oscillatory rods, thus the first and second mechanical resonators, oscillate simultaneously with large oscillation amplitude. This will be described in detail with reference to FIGS. 5 and 6.

In an embodiment, the length L and/or the stiffness of the two rods are selected in such a manner that the oscillation frequency of the first resonator and the the oscillation frequency of the second resonator in the case, in which the oscillatable unit is not covered by medium, have essentially the same value. The resonant frequencies of the first and second resonators are determined by the length as well as the geometric embodiment of the rods and oscillatory rods, and by the type of the connection with the membrane. If one applies, for example, an oscillatory fork, such as used in the LIQUIPHANT instrument sold by the applicant, then, by suitable choice of the length, the diameter, the wall thickness and the embodiment of the connection to the membrane, the resonant frequency of the second mechanical resonator, which includes the rods, can be set.

In another embodiment, the length L and/or the stiffness of the two rods are/is selected in such a manner that the oscillation frequency of the first resonator and the oscillation frequency of the second resonator in the case, in which the oscillatable unit is covered by a selectable reference medium, have essentially the same value. In this way, the sensor can be matched to a certain desired reference medium. The damping of the oscillation amplitude by this medium is thereby counteracted; compare also the following description.

The length of the rods as well as that of the housing can be further optimized with reference to the respective process requirements. If the housing is manufactured from a material distinguished by a good heat insulation, then it has supplementally the function of a temperature isolation tube. The same holds for the rods. Moreover, the length of the rods, and therewith correspondingly also the length of the housing, can be suitably varied. A larger separation from the membrane, thus a spatial separation of the magnets and coil from the membrane, effects a temperature decoupling. In this way, the allowable temperature range can be further expanded beyond that defined by the magnets. Here, it is, however, to be noted that, with increasing length of the rods, the efficiency of the force transfer slightly decreases. Thus, it is necessary to strike a balance between the desired allowable temperature interval and the desired efficiency.

The invention as well as advantageous embodiments thereof will now be described in greater detail based on the appended drawing, FIG. 1-FIG. 6 of which show as follows:

DETAILED DESCRIPTION

Figure 1:
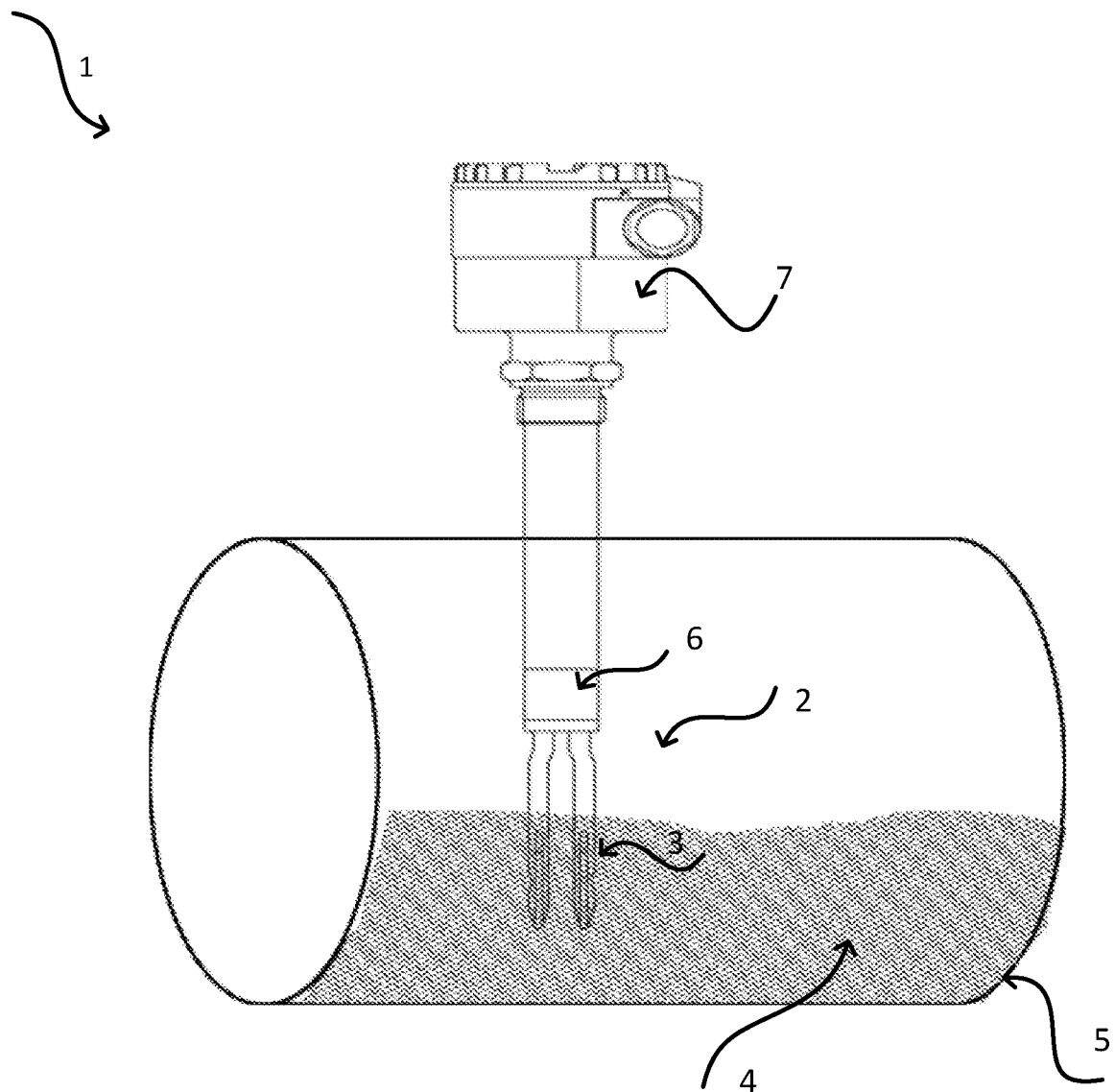
FIG. 1 shows a schematic view of a vibronic sensor according to state of the art.

FIG. 1 shows a vibronic fill-level measuring device 1. A sensor unit 2 with a mechanically oscillatable unit 3 in the form an oscillatory fork penetrates partially into a medium 4, which is located in a container 5. The oscillatable unit 3 is driven by means of the driving/receiving unit 6, as a rule, an electromechanical transducer unit, to execute mechanical oscillations. The driving/receiving unit 6 can be, for example, a piezoelectric stack- or bimorph drive, however, also an electromagnetic or also magnetostrictive driving/receiving unit. However, also other embodiments of a vibronic fill-level measuring device are possible. Additionally shown is an electronics unit 7, by means of which signal registration, —evaluation and/or—feeding occurs.

Figure 2:
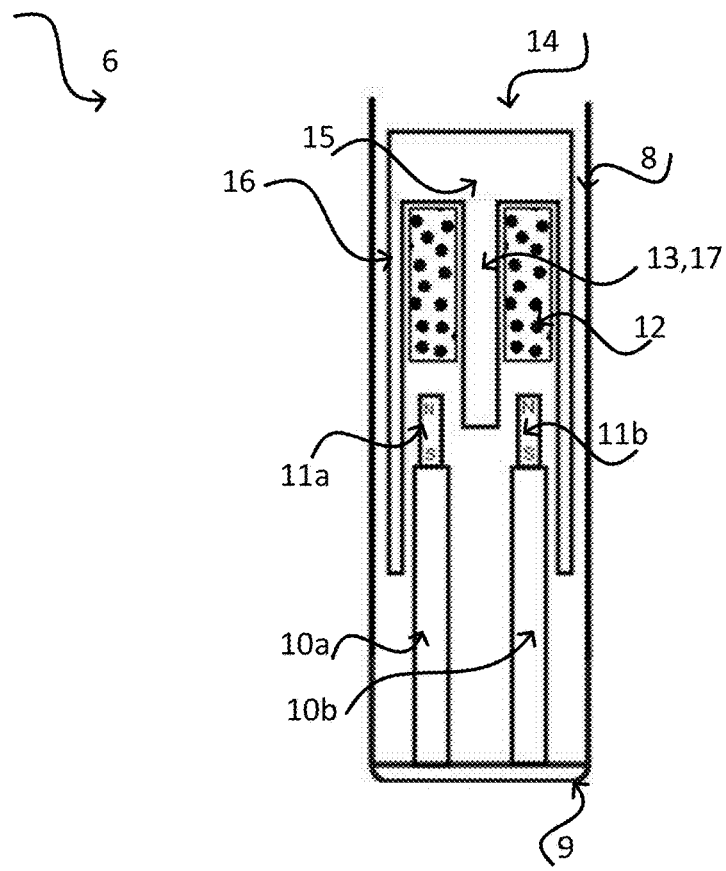
FIG. 2 shows an electromechanical transducer unit of the invention.

FIG. 2 shows schematically an embodiment of an electromechanical transducer unit of the invention. Mounted on the lower end of a housing 8 is a membrane 9. At this location, the housing 8 is thus closed with the membrane 9. In this example, the housing 8 is cylindrical and the membrane 9 disc shaped with circularly round area A. Also other geometries can be used and fall within the scope of the present invention. Extending perpendicularly to the membrane 9 and into the interior of the housing 8 are two rods 10a, 10b secured to the membrane 9. Securement is especially by means of a force transmitting connection. The membrane lies then in a plane perpendicular to the longitudinal direction of the two rods. For example, the two rods 10a, 10b are arranged along an imaginary line through the midpoint of the membrane 9 symmetrically around its midpoint.

Secured in the end region of the rods 10a, 10b away from the membrane 9 is, in each case, a magnet 11a, 11b. Preferably, these are Alnico magnets, especially elongated Alnico magnets.

Arranged above the two magnets 11a, 11b is a coil 12 with core 13. The two rods 10a, 10b with the two magnets 11a, 11b do not contact the coil 12 and the core 13. Coil 12 is supplied with an alternating current signal for producing a magnetic alternating field during operation. Due to this alternating field, the two rods 10a, 10b are deflected via the two magnets 11a, 11b horizontally, i.e. perpendicularly, or transversely, to their longitudinal axis, in such a manner that they are caused to oscillate. On the one hand, the rods 10a, 10b then have a lever action, by which the bending of the rods 10a, 10b produced by the horizontal deflection is transmitted to the membrane 9 in such a manner that the membrane 9 is caused to oscillate. On the other hand, the combination of the two rods 10a, 10b and the membrane 9 form a resonator. The exciting of the membrane 9 to execute mechanical oscillations occurs thus by means of a magnetic alternating field.

The core 13 of the coil 12 is, without limitation to generality, in this example of an embodiment part of a pot-shaped armature unit 14 having a floor 15 as well as a peripheral wall 16. For example, the floor 15 can have a circular cross sectional area same as the area A of the membrane 9. Extending from the floor 15 of the pot-shaped armature unit 14 is the core 13 of the coil 12 in the form of a stub 17 centrally into the interior of the armature unit 14. The peripheral wall 16 has, in this case, then the function of a magnetic field guide back. Armature unit 14 is preferably manufactured of a material of high magnetic permeability, especially of iron, cobalt, or a metal glass.

Figure 3:
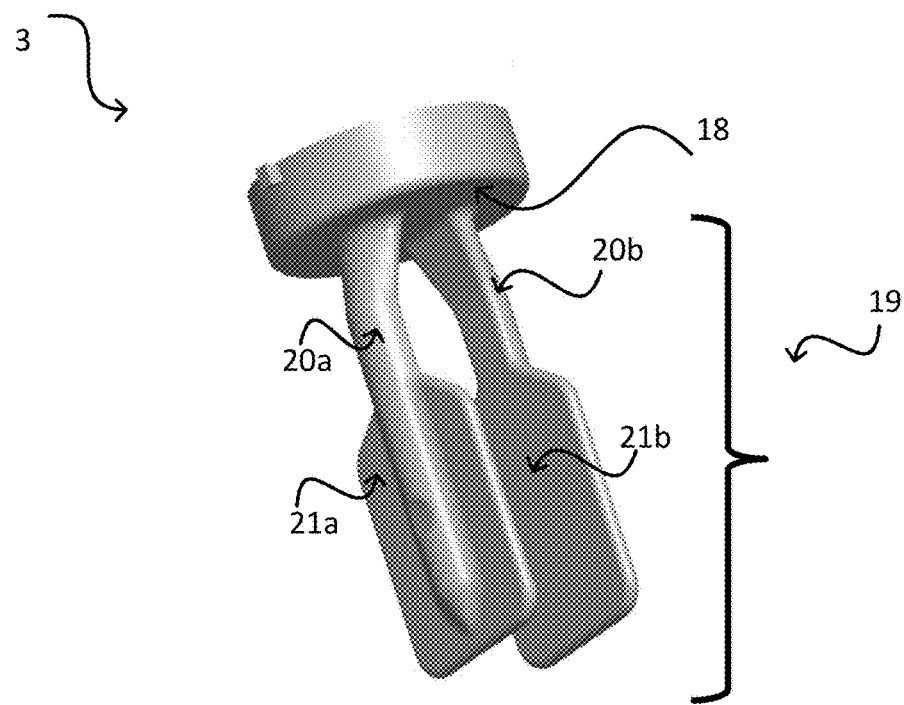
FIG. 3 shows an oscillatable unit in the form of an oscillatory fork.

FIG. 3 shows, by way of example, a schematic view of an oscillatable unit 3 in the form an oscillatory fork, such as is applied for the LIQUIPHANT instrument. Shown is a membrane 18, and the oscillatory element 19 connected therewith. The oscillatory element 19 includes two oscillatory rods 20a, 20b, on which is formed terminally, in each case, a paddle 21a, 21b. In operation, the oscillatory fork 3 executes oscillatory movements corresponding to the oscillatory mode, with which it is driven. Each of the two oscillatory rods 20a, 20b behaves essentially as a so called bending oscillator. In the fundamental oscillation mode, the two oscillatory rods 20a, 20b oscillate, for example, with phase opposite to one another.

Figure 4:
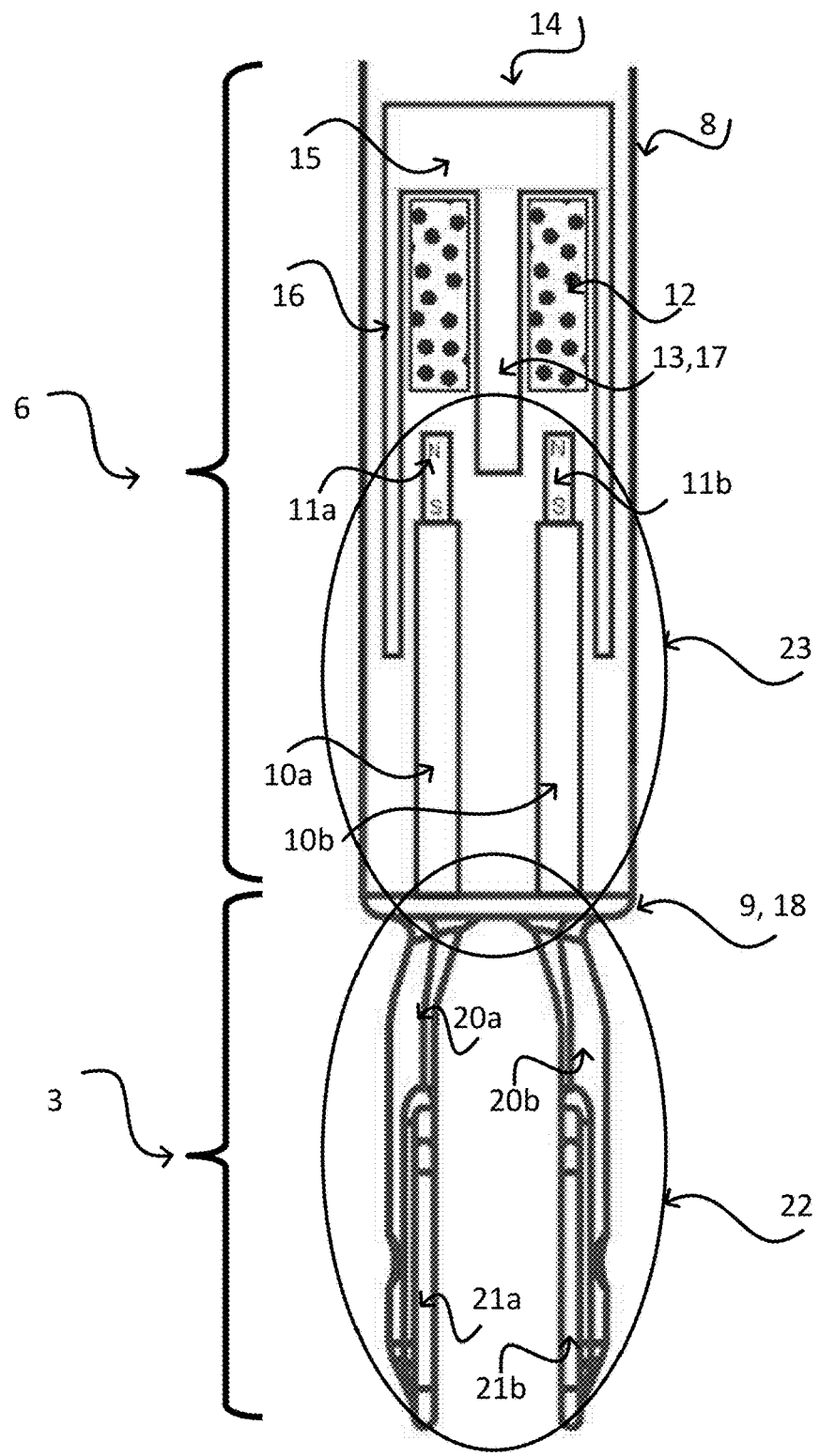
FIG. 4 shows a vibronic fill level measuring device with an oscillatory fork as oscillatable unit and an electromechanical transducer unit of the invention.

FIG. 4 shows, finally, schematically, a vibronic fill-level measuring device with an oscillatable unit 3, as in FIG. 3, and an electromechanical transducer unit, as in FIG. 2. Reference characters already discussed with reference to FIGS. 2 and 3 are, to that extent, not explained again in the following. Membrane 9 of the electromagnetic transducer unit is in this example simultaneously the membrane 18 of the oscillatory fork 3. It is thus a one piece membrane 9,18, which is associated with both the oscillatable unit 3 as well as also the electromechanical transducer unit 6. It is understood, however, that the membrane 9,18 can in another embodiment also be manufactured of two portions 9 and 18 connected with one another for force transmission, wherein the first portion 9 is associated with the electromechanical transducer unit 6, and the second portion 18 is associated with the oscillatable unit 3.

Preferably, the two oscillatory rods 20a, 20b and the two rods 10a, 10b are secured to the membrane in such a manner that, in each case, one rod 10a, 10b and one oscillatory rod 20a, 20b extend along the same longitudinal axis, which is the axis perpendicular to the membrane 9,18. In such case, the two longitudinal axes intersect the plane parallel to membrane 9, 18 with the same separation from the midpoint of the membrane. An increased efficiency can be achieved using this symmetric arrangement.

The two oscillatory rods 20a, 20b of the oscillatable unit 3 form with the membrane 9,18 a first mechanical resonator 22 and the two rods 10a, 10b form with the membrane 9,18 a second mechanical resonator 23. The two resonators 22, 23 are mechanically coupled with one another via the membrane 9,18, wherein the coupling is adjustable via the membrane 9,18. For example, the coupling can be influenced via the thickness, or the material, of the membrane, however, also by the particular connection with the rods 20a, 20b or rods 10a, 10b. In a resonator system coupled in such a manner, two oscillation modes with two different resonance frequencies (F1, F2) occur, which are illustrated in FIGS. 5 and 6.

Figures 5A, 5B:
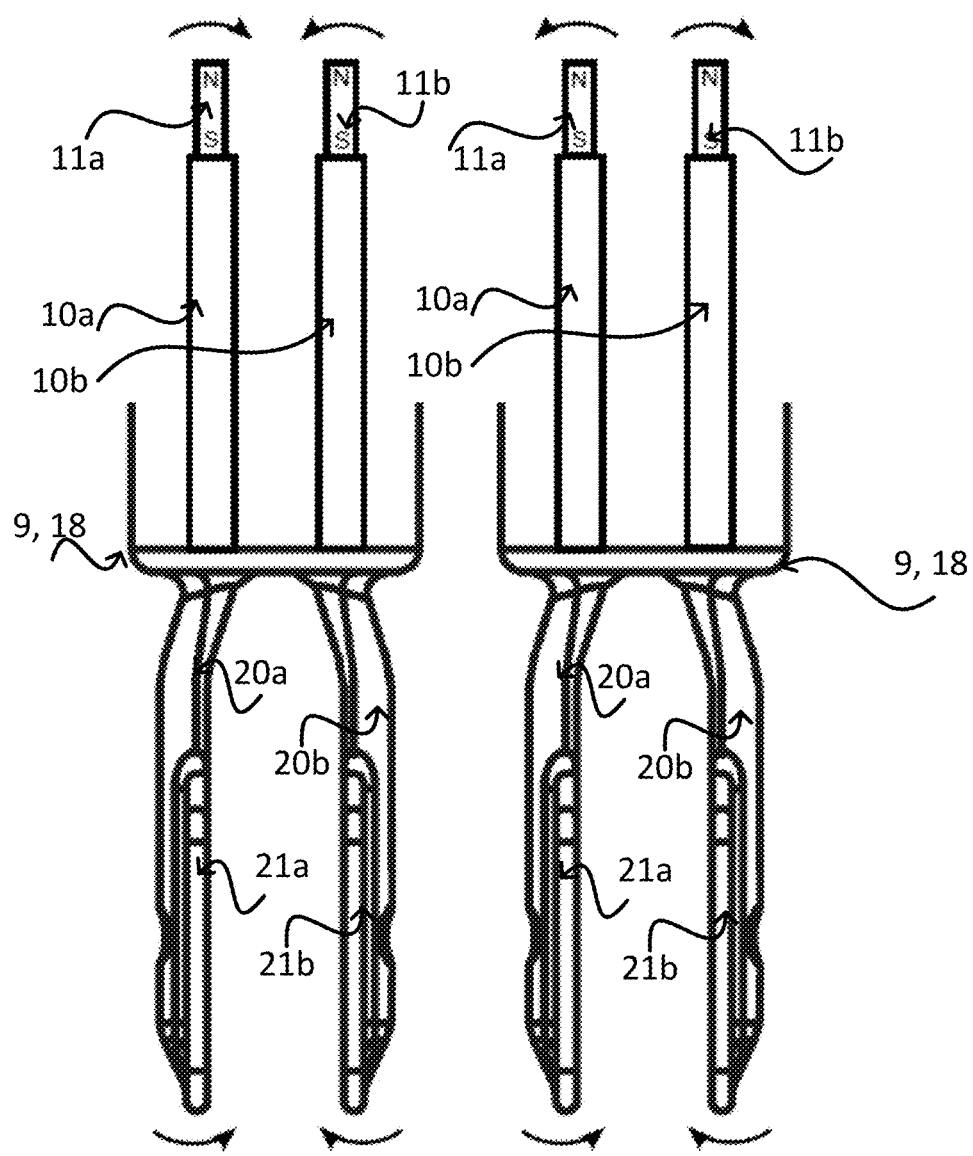
FIG. 5 shows the symmetric (a) and the antisymmetric (b) oscillatory modes of the first and second coupled resonators of the coupled oscillatory system of FIG. 4.

The two oscillation modes are a symmetric oscillatory mode and an antisymmetric oscillatory mode, such as illustrated in FIG. 5. In the case of the symmetric oscillatory mode (FIG. 5a), the first resonator 22 and the second resonator 23 oscillate mirror symmetrically to one another, with reference to the plane of the membrane 9,18. When the rods 10a, 10b move in the end region away from the membrane 9,18 toward one another, then also the two oscillatory rods 20a, 20b in the region of the paddles 21a, 21b move toward one another. In the case of the antisymmetric oscillatory mode (FIG. 5b), in contrast, the rods 10a, 10b in the end region away from the membrane 9,18 move toward one another, when the two oscillatory rods 20a, 20b in the region of the paddles 21a, 21b move away from one another. The antisymmetric oscillatory mode corresponds, in such case, to the natural oscillatory movement of the oscillatory fork 3, for example, an oscillatory fork 3, which is applied in a LIQUIPHANT instrument. In contrast, in the case of the symmetric oscillatory mode, the membrane 9, 18 remains largely unmoved.

If the resonance frequencies F1, F2 of the two oscillation modes lie sufficiently close to one another, the oscillatory rods 20a, 20b and the two rods 10a, 10b in the case, in which the oscillatable unit 3 is not in contact with medium 4, oscillate simultaneously with maximum amplitude with reference to a certain excitation power. Even when the first 22 and the second resonator 23 are embodied in such a manner that the two have as individual systems the same resonant frequency (F1=F2), the coupling of the two resonators 22, 23 by means of the membrane 9, 18 leads to two resonance frequencies (F1≠F2), or oscillation modes, wherein the separation between the two resonance frequencies F1, F2 is determined by the coupling.

Figure 6:
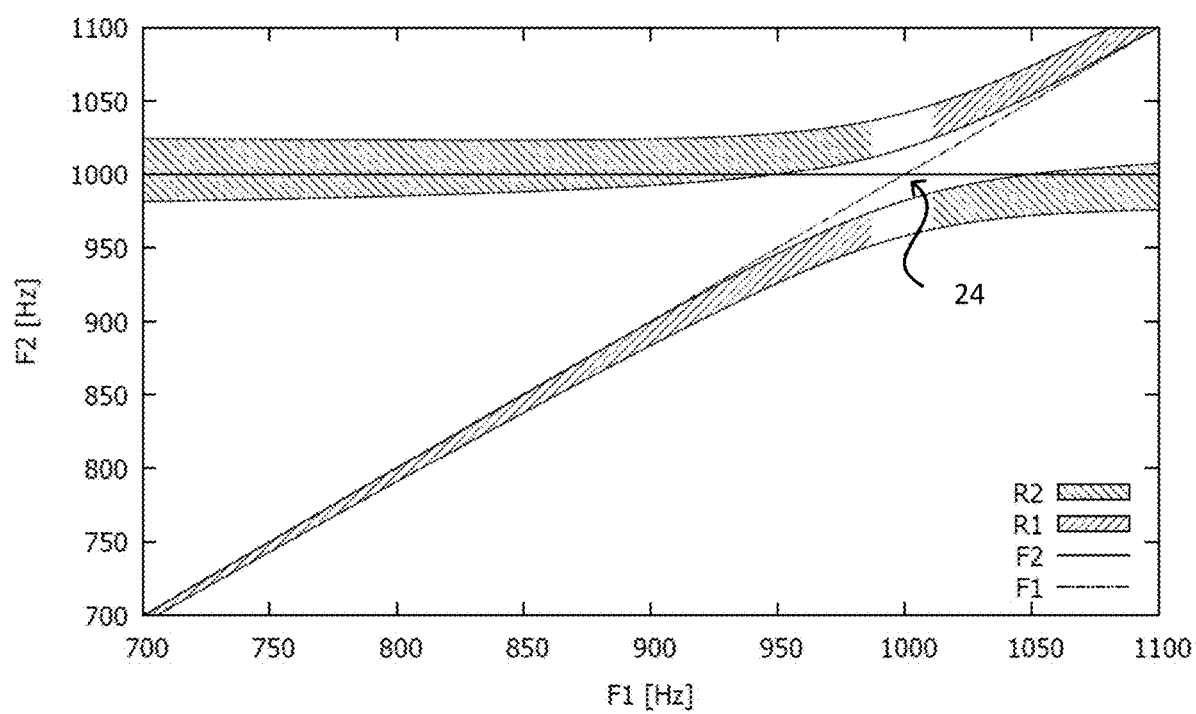
FIG. 6 shows a graph of the two resonance frequencies of the first and second resonators of FIG. 4 or FIG. 5.

FIG. 6 shows a diagram, in which the frequencies of the two resonators 22, 23 are plotted relative to one another. F1 refers to the frequency of the first resonator 22 and F2 to the frequency of the second resonator 23. While the frequency F1 changes upon the immersion of the oscillatable unit 3 in a medium 4, the frequency F2 of the second resonator remains essentially constant. Due to the coupling by the membrane 9,18, there results, however, the two cross hatchings R1 of the first 22 and R2 of the second resonator 23, wherein the width of the cross hatching gives the oscillation amplitudes of the resonators 22, 23. If, for example, the first resonator 22, thus the oscillatable unit 6, oscillates with a frequency F1=700 Hz, then the oscillatory movement occurs with a comparatively small oscillation amplitude. In such case, let us assume that the oscillation at F1=700 Hz corresponds to an oscillation of the oscillatable unit 3 in the case of partial immersion in a certain medium 4. If the second resonator 23 oscillates simultaneously at F2=1000 Hz, then this oscillation has a comparatively large oscillation amplitude. If then the oscillatable unit 3 is slowly pulled out of the medium 4, both the frequency F1 of the first resonator 22 as well as also its oscillation amplitude R1 increase. For purposes of simplification, let us for this consideration neglect the lessening medium damping resulting from the withdrawal of the oscillatable unit 3 from the medium 4. As a consequence, the coordination of the two resonators 22, 23 improves and more energy can be transmitted from the rods 10a, 10b to the oscillatory rods 20a, 20b. To the same degree, however, the oscillation amplitude R2 of the second resonator 23 decreases.

At the point of intersection 24, the first 22 and the second resonator 23 are matched to one another. In spite of this, due to the coupling by the membrane 9, 18, two different resonance frequencies F1 and F2 occur. Since in this region, no associating of the resonances to the rods 20a, 20b, and rods 10a, 10b, is possible, no crosshatching is provided in this region. If the frequency F2 of the first resonator 22 rises further, then a behavior mirror symmetrical to the point of intersection 24 results for the two oscillation modes of the first 22 and second 23 resonators.

Preferably, the length of the two rods 10a, 10b should be selected in such a manner that the lever action on the membrane 9,18 is as large as possible. At the same time, however, attention should be paid that no too great separation between the resonance frequencies (F1, F2) of the first 22 and second 23 resonator arises, in order to achieve an as efficient as possible energy transmission from the electromechanical transducer unit 4 to the oscillatory rods 20a, 20b with the paddles 21a, 21b, thus an as large as possible efficiency. On the other hand, the resonant frequency F2 of the second resonator 23 should, however, also not lie in the dynamic range of the resonant frequency F1 of the oscillatable unit 3, in order that no doubled associating of a frequency can occur. The terminology, dynamic range, refers, in such case, to the interval of resonance frequencies F1, with which the oscillatable unit 3 can oscillate in the case of contact with different media 4 and in the case of different immersion depths in the particular medium 4. It follows therefrom that the resonant frequency F2 of the second resonator 23 is to be chosen such that it lies just above the highest frequency F1 of the dynamic range of a certain oscillatory mode of the oscillatable unit 3. At the same time, it is important so to optimize the stiffness and mass of the rods 10a, 10b that an as large as possible lever action is present. If, for example, a LIQUIPHANT oscillatory fork is used, then, without contact with the medium to be measured, F1≈1000 Hz. Then, the second resonator 23 is tuned, for example, to a frequency of F2≈1100 Hz, so that, from the coupling, the frequency F2 of the second resonator 23 sinks to about 950 Hz. During immersion in a medium to be measured, the frequency F1 of the first resonator 22 decreases, while the frequency F2 of the second resonator 23 remains essentially constant.

For example, the matching of the resonance frequencies F1 and F2 can be performed in such a manner that these be matched to one another without contact of the oscillatable unit 3 with a medium 4. In this case, the frequencies F1 and F2 shift away from the point of intersection 24 in the case of at least partial immersion of the oscillatable unit in a medium 4. On the other hand, the matching of the resonance frequencies F1 and F2 can also be performed in such a manner that they are matched to one another in the case of a certain immersion depth of the oscillatable unit 3 in a selectable reference medium 4. In this case, the type of matching of the two resonators 22, 23 to one another counteracts the damping by the reference medium.

LIST OF REFERENCE CHARACTERS 1 vibronic sensor
2 sensor unit
3 oscillatable unit
4 medium
5 containment
6 driving/receiving unit
7 electronics unit
8 housing of the driving/receiving unit
9 membrane of the driving/receiving unit
10a, 10b rods
11a, 11b magnets
12 coil
13 core
14 armature unit
15 floor
16 peripheral wall, magnetic guide back
17 stub of the armature unit, simultaneously, in given cases, core of the coil
18 membrane of the oscillatable unit
19 oscillatory element
20a, 20b oscillatory rods
21a, 21b paddles
22 first resonator
23 second resonator
24 point of intersection
F1 frequency of the first resonator
F2 frequency of the second resonator
R1 oscillation amplitude of the first resonator
R2 oscillation amplitude of the second resonator
L length of the rods
λ wavelength of the waves propagating along the rods.

The invention claimed is:

1. An electromechanical transducer unit for a field device of automation technology, comprising:
a membrane embodied to execute mechanical oscillations;
two rods, each extending perpendicular to the membrane and secured to the membrane at a proximal end;
a housing, wherein the membrane forms at least one portion of a wall of the housing and wherein the two rods extend into the housing interior;
two magnets, each magnet secured in an end region opposite the membrane to a different one of the two rods at a corresponding distal end; and
a coil with a core, the coil secured adjacent the magnets within the housing opposite the two rods and contactable with an electrical, alternating current signal,
wherein the coil is configured to produce a magnetic field that causes the two rods, via the two magnets, to execute mechanical oscillations perpendicular to the longitudinal axis of the two rods such that the distal ends of two rods oscillate toward and away from each other, and
wherein the two rods are secured to the membrane such that oscillations of the membrane result from the oscillations of the two rods.

2. The electromechanical transducer unit of claim 1, wherein the magnets are Alnico magnets.

3. The electromechanical transducer unit of claim 1, wherein the core of the coil is a part of a pot-shaped armature unit having a floor, a peripheral wall and a stub extending centrally from the floor into the interior of the armature unit, wherein the stub forms the core of the coil, and wherein the peripheral wall serves as a magnetic field guide back.

4. The electromechanical transducer unit of claim 3, wherein the armature unit is composed of a material with relatively high magnetic permeability or of a metallic glass.

5. The electromechanical transducer unit of claim 4, wherein the material is iron, cobalt or cobalt iron.

6. The electromechanical transducer unit as claimed in claim 3, wherein the two magnets extend contactlessly into the pot-shaped armature unit and are disposed at the same separation distance from the coil on oppositely lying sides when no magnetic field is present.

7. An apparatus for determining and/or monitoring at least one process variable of a medium in a containment, comprising:
a sensor unit including at least one electromechanical transducer unit, each electromechanical transducer unit including:
a membrane embodied to execute mechanical oscillations;
two rods, each extending perpendicular to the membrane and secured to the membrane at a proximal end;
a housing, wherein the membrane forms at least one portion of a wall of the housing and wherein the two rods extend into the housing interior;
two magnets, each magnet secured in an end region opposite the membrane to a different one of the two rods; and
a coil with a core, the coil secured adjacent the magnets within the housing opposite the two rods and contactable with an electrical, alternating current signal,
wherein the coil is embodied to produce a magnetic field that causes the two rods, via the two magnets, to execute mechanical oscillations perpendicular to the longitudinal axis of the two rods such that the distal ends of two rods oscillate toward and away from each other, and wherein the two rods are secured to the membrane such that oscillations of the membrane result from the oscillations of the two rods; and an electronics unit, wherein the at least one electromechanical transducer unit is embodied to excite the sensor unit to execute mechanical oscillations using an electrical excitation signal in the form a first electrical, alternating current signal supplied to the coil, to receive mechanical oscillations of the sensor unit, and to convert the oscillations of the sensor unit into an electrical, received signal in the form of a second electrical, alternating current signal, and wherein the electronics unit is embodied to produce the exciter signal starting from the received signal, and to determine the at least one process variable at least based on the received signal.

8. The apparatus of claim 7, wherein the sensor unit includes an oscillatable unit connected to the at least one electromechanical transducer unit.

9. The apparatus of claim 8, wherein the oscillatable unit includes at least one portion of the membrane, or at least one portion of the membrane and at least one oscillatory rod secured thereto.

10. The apparatus of claim 8, wherein the membrane has two portions connected to one another by a force-transmitting connection, wherein a first portion is associated with the electromagnetic transducer unit and a second portion is associated with the oscillatable unit.

11. The apparatus of claim 8, wherein the oscillatable unit is arranged in a defined position within the containment such that it descends to a determinable immersion depth in the medium.

12. The apparatus of claim 8, wherein the oscillatable unit is an oscillatory fork with two rods, and wherein the two rods of the electromechanical transducer unit secured to the membrane and the two oscillatory rods secured to the membrane are arranged oppositely lying and mirror symmetrically to one another with reference to a plane perpendicular to a longitudinal axis through the rods and/or oscillatory rods.

13. The apparatus of claim 12, wherein the two oscillatory rods and the membrane form a first mechanical resonator, the two rods of the electromechanical transducer unit and the membrane form a second mechanical resonator, and the first and second resonators are mechanically coupled with one another via the membrane, and wherein the frequency of the excitation signal is selected in such a manner that the first and second resonators oscillate in an antisymmetric, oscillatory mode with reference to a plane through the membrane perpendicular to the longitudinal axis of the rods and/or oscillatory rods.

14. The apparatus of claim 13, wherein the two rods have substantially the same length and/or stiffness, and wherein the length and/or stiffness of the two rods is selected such that an oscillation frequency of the first resonator and an oscillation frequency of the second resonator have essentially the same value when an oscillatable unit of the sensor unit is not covered by the medium.

15. The apparatus of claim 13, wherein the two rods have substantially the same length and/or stiffness, and wherein the length and/or stiffness of the two rods is selected such that an oscillation frequency of the first resonator and an oscillation frequency of the second resonator have essentially the same value when an oscillatable unit of the sensor unit is covered by a predetermined reference medium.

16. The apparatus of claim 7, wherein the process variable is a fill level or flow of the medium in the containment, or a density or viscosity of the medium.

* * * * *